United States Patent
Li et al.

(10) Patent No.: US 8,574,624 B2
(45) Date of Patent: Nov. 5, 2013

(54) HIGHLY INHIBITED STARCH FILLERS FOR FILMS AND CAPSULES

(75) Inventors: Zhixin Li, Bridgewater, NJ (US); Michele Merrette Shore, Bound Brook, NJ (US); Ralph Trksak, Manville, NJ (US)

(73) Assignee: Corn Products Development, Inc., Sao Paulo (BR)

( * ) Notice: Subject to any disclaimer, the term of this patent is extended or adjusted under 35 U.S.C. 154(b) by 750 days.

(21) Appl. No.: 11/600,980

(22) Filed: Nov. 17, 2006

(65) Prior Publication Data

US 2008/0138402 A1    Jun. 12, 2008

(51) Int. Cl.
A61K 47/26 (2006.01)
A61K 9/48 (2006.01)
A23L 1/0522 (2006.01)

(52) U.S. Cl.
USPC ............................ 424/451; 514/778; 426/103

(58) Field of Classification Search
None
See application file for complete search history.

(56) References Cited

U.S. PATENT DOCUMENTS

| | | | |
|---|---|---|---|
| 4,465,702 A | 8/1984 | Eastman et al. | |
| 4,477,480 A | 10/1984 | Seidel et al. | |
| 5,037,929 A | 8/1991 | Rajagopalan et al. | |
| 5,131,953 A | 7/1992 | Kasica et al. | |
| 5,149,799 A | 9/1992 | Rubens | |
| 5,187,272 A | 2/1993 | Katcher et al. | |
| 5,362,777 A | 11/1994 | Tomka | |
| 5,660,900 A * | 8/1997 | Andersen et al. | 428/35.6 |
| 5,725,676 A | 3/1998 | Chiu et al. | |
| 6,790,495 B1 | 9/2004 | Tomka et al. | |
| 6,949,256 B2 * | 9/2005 | Fonkwe et al. | 424/451 |
| 2003/0138482 A1 | 7/2003 | Fonkwe | |
| 2005/0084516 A1 | 4/2005 | Ballard et al. | |
| 2005/0196436 A1 * | 9/2005 | Chantranukul et al. | 424/451 |
| 2006/0204597 A1 | 9/2006 | Bird et al. | |
| 2008/0138402 A1 * | 6/2008 | Li et al. | 424/451 |

FOREIGN PATENT DOCUMENTS

| | | |
|---|---|---|
| EP | 0304401 A2 | 2/1989 |
| EP | 0304401 A2 | 8/1989 |
| EP | 0554818 | 8/1993 |
| EP | 1103565 | 5/2001 |
| EP | 1260218 A2 | 11/2002 |
| EP | 1260218A2 A2 | 11/2002 |
| EP | 1 264 882 A2 | 12/2002 |
| EP | 1 317 916 A2 | 6/2003 |
| EP | 1510527 | 3/2005 |
| EP | 1570843 | 9/2005 |
| EP | 1589067 | 10/2005 |
| EP | 1 723 853 A2 | 11/2006 |
| EP | 1792939 | 6/2007 |
| JP | 2005 245393 A | 9/2005 |
| JP | 2007-56206 A | 3/2007 |
| WO | WO0191721 | 12/2001 |

OTHER PUBLICATIONS

Arvanitoyannis et al. Carbohydrate Polymers. 1998; 36: 105-119.*
Translation of Yoshifumi et al. JP 2007-56206 Mar. 8, 2007.
Corresponding Chinese Office Action. Dated Dec. 6, 2010.
Nilsson A.C. et al (2008) "Including indigestible carbohydrates in the evening meal of healthy subjects improves glucose tolerance, . . . " J Nutr. 138(4):732-9.
Translation of Japan Office Action of Oct. 9, 2012.

* cited by examiner

Primary Examiner — Shanon A Foley
(74) Attorney, Agent, or Firm — Thomas C. McKenzie; Karen Kaiser

(57) ABSTRACT

The invention provides the addition of highly inhibited starch filler to gelatin-free films and soft capsules. The addition of the highly inhibited starch filler raises the solid levels during processing without substantially increasing the melt viscosity. The resultant films and capsules are transparent.

18 Claims, No Drawings

HIGHLY INHIBITED STARCH FILLERS FOR FILMS AND CAPSULES

FIELD OF THE INVENTION

The invention relates to films and capsules that are essentially gelatin-free. The films and capsules comprise a matrix starch and highly inhibited starch filler.

BACKGROUND OF THE INVENTION

Gelatin is used in various pharmaceutical and nutraceutical products, including soft gelatin capsules and hard gelatin capsule shells as well as many different food applications. Soft gelatin capsules are typically used to encapsulate a solution or dispersion of, for example, a nutritional or pharmaceutical active agent in a liquid carrier, and have many advantages over other dosage forms, permitting accurate delivery of a unit dose in an easy-to-swallow, transportable, essentially tasteless form. However, gelatin has many drawbacks, including the cost and continuity of a safe supply.

Conventional fillers have been added to gelatin free films and capsules to increase the solid loading in order to improve the quality of throughput in the manufacturing process. However, the addition of conventional fillers results in translucent and even opaque films and capsules. In the case of traditional fillers with a high refractive index, such as calcium carbonate and titanium oxide, there is a negative effect on film transparency even at low concentrations. Most of these fillers have a whitening effect. Other traditional fillers produce unacceptable melt viscosities or undesirable film quality.

There continues to be a need in the art for substantially gelatin-free composition for pharmaceutical, nutraceutical and food application systems that increases the total solids loading while maintaining transparency. The present invention addresses this need.

SUMMARY OF THE INVENTION

The present invention provides transparent film and capsule compositions having similar textural and functional properties compared to gelatin and can be used as a replacement therefor. The present composition increases solid loading of the film composition while maintaining film transparency.

One embodiment of the invention provides a starch-based composition that comprises at least one highly inhibited starch filler and at least one matrix starch. One preferred composition comprises highly inhibited waxy rice and/or corn starch fillers and a matrix starch. If desired, other ingredients, such as, gums, plasticizers, salts, cations, emulsifiers, fragrances, humectants, surfactants, colorants, taste masking agents (e.g. flavor or sweetener), permeation enhancers or other surface modifying agent, and/or the like may be included. In one preferred embodiment the composition is a film composition. In another preferred embodiment the composition is a capsule composition.

Another embodiment of the invention provides a method of producing transparent starch films by adding a highly inhibited starch filler. The presence of the highly inhibited starch filler granules within the film network does not interfere with normal film transparency of the starch.

Yet another embodiment of the invention provides improved film strength. Performance such as capsule burst strength is improved.

DETAILED DESCRIPTION OF THE INVENTION

A film is defined herein as a flexible product formed, for example, by casting, extruding or blowing, a flowable composition comprising film forming ingredients, and a carrier liquid such as water onto a substrate surface. A film will typically but not necessarily have a uniform thickness and will generally vary in thickness from about 0.02 mm to about 1.8 mm. The film can be formed or processed to have a variety of lengths, widths and shapes depending upon the desired end use application.

A soft capsule is defined herein as a soft soluble container in which an active is enclosed. Soft capsules may be produced from films using rotary die and/or drum casting processes known in the art. Soft capsules can also be produced directly from the film forming ingredients by means of extrusion processes known in the art.

An essentially gelatin-free composition and substantially gelatin-free composition, herein used interchangeably, is defined as composition containing less than 1 total dry weight percent of gelatin.

Cooking is herein defined as heating a sample at a temperature of 95-100° C. in deionized water for 30-60 minutes.

Slurry is herein defined as a suspension of starch granules in water.

Dry weight percent is herein defined as weight not including water.

The films and the soft capsules of the invention comprise at least one highly inhibited starch filler and at least one matrix starch.

Highly Inhibited Starch Filler

Inhibited starch filler is the modification of starch to improve process tolerance to temperature, pH and shear through control of granular swelling under adverse conditions. There are various methods to form highly inhibited starch fillers. Non-limiting examples of highly inhibited starches include crosslinking starch with chemical treatments such as phosphorus oxychloride, sodium trimetaphosphate, epichlorohydrin, and mixtures of adipic anhydride and acetic anhydride. Other non-limiting methods of inhibition include physical (heat or radiation) treatments of starch.

Highly inhibited starch fillers may be made from starch including, without limitation, waxy rice, corn, high amylose corn, waxy maize, tapioca, wheat, sago and potato starch. Other suitable highly inhibited starch fillers may be made from waxy maize starch derived from a plant which is heterozygous for the recessive sugary-2 allele. Particularly suitable highly inhibited starch fillers are waxy rice and corn starch.

Suitable inhibited starch filler that are useful in the practice of the invention swell less than about 150% in their original granule size after cooking. As the extent of inhibition of starch increases, the starch granules swell less during the cooking process. The percent swelling is inversely proportional to the extent of inhibition of starch filler.

In one aspect of the embodiment, the size of the highly inhibited starch filler ranges from about 1 µm to about 50 µm after cooking. In another embodiment, the size of the highly inhibited starch filler ranges from about 1 µm to about 35 µm after cooking.

Suitable highly inhibited starch fillers that are also useful in the practice of the invention, cooked at 10% solids in water and then cooled to room temperature, have a viscosity less than 100 cP at 22.5° C. and 1-100 1/sec shear rate. The viscosity of the highly inhibited starch filler is significantly lower than the un-inhibited starch under the same cooking condition. The highly inhibited starch filler can raise the solids levels during processing without substantially increasing the viscosity of a film forming melt, and hence, the highly inhibited starch filler may be added at any time during the process.

For highly inhibited starch fillers produced from phosphorus reactions, bound phosphorous content may be used to determine the extent of inhibition. As the extent of inhibition in starch increases, the percent bound phosphorus increases. The percent bound phosphorus is proportional to the extent of inhibition of starch. Suitable fillers that are useful in the practice of the invention should have at least 0.10% bound phosphorus. However, this method of determining the extent of inhibition is limited to fillers inhibited with a phosphorus-containing reagent.

The films and the soft capsules will typically comprise from about 0.1 to about 20 dry weight percent of the inhibited fillers. In another embodiment, the film and capsule will comprise from about 0.5 to 15 total dry weight percent, based on the total composition, of highly inhibited starch fillers.

Matrix Starch

The matrix starch may be a native starch or a modified starch. Modified starch, as used herein, is intended to include starches which have been modified physically, chemically and/or by hydrolysis.

Useful matrix starch includes starches such as maize or corn, waxy maize, potato, cassava, tapioca and wheat starch. Other starches include varieties of rice, waxy rice, pea, sago, oat, barley, rye, amaranth, sweet potato, and hybrid starches available from conventional plant breeding, e.g., hybrid high amylose starches having amylose content of 40% or more, such as high amylose corn starch. Also useful matrix starches are high amylose potato and waxy potato starches. Another suitable matrix starch is waxy maize starch derived from a plant which is heterozygous for the recessive sugary-2 allele.

The matrix starches may be physically modified, e.g., by extrusion, spray-drying, drum-drying, agglomeration and/or pregelatinization. The starch may be pregelatinized for immediate use in preparing the film composition. In one aspect, pregelatinized starch is pregelatinized waxy corn starch, available from National Starch and Chemical Company. The starches may be pregelatinized using techniques known in the art and disclosed for example in U.S. Pat. Nos. 4,465,702, 5,037,929, 5,131,953, and 5,149,799. Also see, Chapter XXII—"Production and Use of Pregelatinized Starch", *Starch: Chemistry and Technology*, Vol. III—Industrial Aspects, R. L. Whistler and E. F. Paschall, Editors, Academic Press, New York 1967. Alternatively, the starch may be pregelatinized and then stored for later use in preparing the film forming composition. Physical modification includes by shearing or thermal-inhibition, for example by the process described in U.S. Pat. No. 5,725,676.

The matrix starch may also be chemically modified, including without limitation, inhibited, acetylated, organically esterified, hydroxyethylated, hydroxypropylated, phosphorylated, inorganically esterified, cationic, anionic, non-ionic, and zwitterionic, and succinate (succinylated) and substituted succinate derivatives thereof. Such modifications are known in the art, for example in *Modified Starches: Properties and Uses*, Ed. Wurzburg, CRC Press, Inc., Florida (1986). Particularly suitable starches, without limitation, include hydroxyalkylated starches such as hydroxypropylated or hydroxyethylated starches, and succinated (succinylated) starches such as octenylsuccinated (octenylsuccinylated) or dodecylsuccinated (dodecenylsuccinylated) starches. One suitable type of starch is hydroxypropylated starch available from National Starch and Chemical Company. Other suitable starches are waxy starches, also available from National Starch and Chemical Company. As used herein, the term "waxy" is intended to include a starch containing at least about 95% by weight amylopectin. In another embodiment, starches are low amylose starches. As used herein, the term "low amylose" is intended to include starches containing less than 40% by weight amylose.

The matrix starches may also be converted or hydrolyzed, and suitable starches include fluidity or thin-boiling starches prepared by oxidation, acid hydrolysis, enzyme hydrolysis, heat and or acid dextrinization. These processes are well known in the art.

Any starch having suitable properties for use herein may be purified by any method known in the art to remove undesirable flavors and colors that are native to the polysaccharide or created during processing. Suitable purification processes for treating starches are disclosed in the family of patents represented by EP 554 818 (Kasica, et al.). Alkali washing techniques, for starches intended for use in either granular or pregelatinized form, are also useful and described in the family of patents represented by U.S. Pat. No. 4,477,480 (Seidel) and U.S. Pat. No. 5,187,272 (Bertalan et al.).

Suitable matrix starches have a water fluidity in the range of about 30 to about 90, more particularly, in the range of about 45 to about 85. Water fluidity is known in the art and, as used herein, is measured using a Thomas Rotational Shear-type Viscometer (commercially available from Arthur A. Thomas Co., Philadelphia, Pa.), standardized at 30° C. with a standard oil having a viscosity of 24.73 cps, which oil requires 23.12±0.05 sec for 100 revolutions. Accurate and reproducible measurements of water fluidity are obtained by determining the time which elapses for 100 revolutions at different solids levels depending on the starch's degree of conversion: as conversion increases, the viscosity decreases. The conversion may be by any method known in the art including oxidation, enzyme conversion, acid hydrolysis, heat and/or acid dextrinization.

The matrix starches may be used in any amount necessary to achieve the desired viscosity and thickness. In one embodiment, the total starch will be used in an amount of about 40% to about 95%, in another embodiment, from 50% to 90%, by dry weight of the film and/or soft capsule composition.

Other Components

The films and the soft capsules composition of the invention may further include at least one plasticizer. The plasticizer used will depend in part upon the end use application and is intended to include, without limitation, glycerin, sorbitol, sorbitol esters, maltitol, mannitol, xylitol, erythritol, lactitol, propylene glycerol, polyethylene glycol, diethylene glycol, mono acetate of glycerol, diacetate of glycerol, triacetate of glycerol, sucrose, fructose, invert sugars, corn syrup, saccharide oligomers, 1,2-propylenglycol, mono-, di- or tri-acetates of glycerol, and mixtures thereof. In one suitable embodiment, the plasticizers include glycerin and sorbitol. The plasticizer may be used in any amount necessary to achieve the desired plasticizing effect. The plasticizer may be used in an amount of about 5% to about 50%, more preferably from about 10% to about 45%, by dry weight of the total composition.

The films and the soft capsules composition may also include a blend of gums or hydrocolloids. Exemplary gums and hydrocolloids which may be used in the present invention include, without limitation, gellan gum, xanthan gum, tragacanth gum, guar gum, locust bean gum, acacia gum, gum Arabic, carrageenan, and galactomanans. One suitable gum is gellan gum. Gellan gum may be added to the film forming composition to increase the elasticity and the rigidity, depending upon the level of acyl content of the gum. A blend of a high acyl gellan and a low acyl gellan gum may be used in any amount necessary to achieve the desired gel strengthening effect. As used herein, high acyl content is intended to mean more than 40% acetyl and more than 45% glyceryl residual substituents per repeat unit. As used herein, low acyl content is intended to mean less than 25% acetyl and less than 15% glyceryl residual substituents per repeat unit. The gellan gum is also present to allow heat reversibility of the system, which may be enhanced by decreasing the amount of low acyl gellan to the lower end of the range. The gums or hydrocolloids may be used in any amount necessary to achieve the desired elasticity and rigidity. Particularly, gellan gum may be used up to 20% of the total dry weight of the composition.

The films and the soft capsules composition may also contain other optional or desired components such as, without limitation, salt buffer, emulsifiers, humectants, surfactants, preservatives, embrittlement inhibiting agents, disintegrants, colorants, taste masking agents such as a flavor or sweetener, permeation enhancers and surface modifying agents. Salt buffers can improve the burst strength of the soft capsules. Possible salt buffers are, but not limited to, sodium citrate, potassium citrate, sodium phosphate dibasic, and sodium acetate. These optional components are typically added in minor amounts, particularly less than about 10 dry weight % of the film. More preferably, less than about 5 dry weight % of the composition of the optional components may be used.

Method of Producing Films and Capsules

The highly inhibited starch fillers and matrix starch are added to water to form a solids concentration suitable for a film or capsule shell process. For casting of a hot liquid on a cold drum, the concentration is typically suitable at about 20% to about 70% solids and about 80% to about 30% water. It is generally understood that hard capsules have lower solids level and soft capsules have higher solids level. Because the highly inhibited starch filler granules do not swell appreciably during the cooking process and maintain their small granular size, higher levels of solids may be added to the melt without increasing the overall viscosity. Other methods known in the art for forming a film may be used including without limitation extrusion, either direct or from pre-made pellets. The film may be made during the encapsulation process or may be pre-made for later use. The blend of starch and highly inhibited starch fillers can be prepared, and dried to form a film. This can later be formed into soft capsules with heat, water, and/or radiation.

The film's attributes allow it to be used to form gelatin-free capsule shells using techniques known in the art, including a rotary machine. After filling, the capsules may be dried using techniques conventional in the art, including tray drying.

Capsule shells made using the rotary die process will be similar in look and feel to gelatin capsule shells, having a wet thickness of about 0.25 to about 1.8 mm, in another embodiment about 0.5 to about 1.4 mm. The fill materials for the soft capsule may be pharmaceutical, nutraceutical, and/or food agent. The fill materials for the soft capsule shells may be any of those typically used in the art, including oils, hydrophobic liquids and emulsions containing active agents. Fill materials may include cosmetics, bath oils, foods, vitamins, detergents, liquids, semisolids, suspensions, flavorings and pharmaceuticals.

Films made from the above highly inhibited starch fillers and matrix starch result in a film that is flexible, smooth and transparent. The presence of the highly inhibited starch filler granules within the film network do not interfere with film transparency. Film transparency is defined as the degree of transparency to light and is used herein as an indicator of film clarity. Typically, the addition of fillers into a clear film reduces film transparency due to scattering of light. Scattering occurs at the filler-film matrix interface, and the amount of light scattered increases as a function of filler loading, filler size, and (the second power of) filler differential index of refraction with respect to the matrix.

Suitable dry films have a percent film transparency greater than 50% at a thickness of about 0.50 mm to about 0.65 mm. In other embodiments, suitable dry films have a percent film transparency greater than 70% at about 0.50 mm to about 0.65 mm.

The invention also provides capsules having improved film strength, e.g. improvement of capsule burst strength. The burst strength is defined as the force required to break a capsule.

The invention will be described further in the following examples, which are included for purposes of illustration and are not intended, in any way, to be limiting of the scope of the invention.

EXAMPLES

Example 1

Preparation of Highly Inhibited Starch Filler

The inhibition conditions of Samples 1-12 are listed in Table I. The inhibition of waxy rice starch filler of Example 12 is discussed in detail. A slurry was prepared with two kilograms of waxy rice starch in 3000 mL of tap water. To the slurry, 12% of a 99:1 blend of sodium trimetaphosphate (STMP, food grade, Chemische Fabrik Budenheim KG) and sodium tripolyphosphate (STPP, food grade, Chemische Fabrik Budenheim KG), based on the weight of starch, were added and reacted for three hours. The slurry was then neutralized, filtered, washed to remove unbound phosphate salt, and air dried.

Example 2

Filler Inhibition Analysis

To determine the extent of inhibition of the starch filler, the percent change in swelling was measured. The uncooked filler slurry was measured using a Horiba LA-900 Laser Scattering Particle Size Distribution Analyzer. The inhibited fillers were then cooked at 95-100° C. for 30 minutes in deionized water and the swollen granules were measured using the same Horiba LA-900 Laser Scattering Particle Size Distribution Analyzer. The percent swelling of the filler granules is reported in Table I.

Viscosity of the filler samples in water was also measured to express the extent of starch inhibition. Static shear viscosities of inhibited starch fillers were measured using a Rheometrics RFSII with Couvette geometry, a rate sweep of 1-100 1/s, and a temperature of 22.5° C. Filler samples were prepared by cooking a 10% solids slurry of the dry fillers in deionized water in a water bath at 95-100° C. for 30 minutes. The cooked slurry was preconditioned to about 22.5° C. and premixed thoroughly before charging to the couvette. The sample was pre-sheared for 15 seconds before data collection. Viscosity was recorded at 100 rad. The viscosity of the filler slurry is reported in Table I.

To determine the bound phosphorus content, a mixture of 10.00 g of the inhibited filler and 600 mL of 5% EDTA (Sigma-Aldrich Corp. St. Louis, Mo.) solution was mixed for five minutes using a magnetic mixer. This method was used to determine the extent of inhibition only when STMP and STPP reagents were used to crosslink the starch. This mixture was then filtered using a Büchner funnel and 11 cm Whatman #1 filter paper. Before the starch cake cracked, four 200 mL aliquots of purified water were poured continuously over the starch cake, and the sides of the Büchner funnel were also washed down with the purified water. To perform a hydrolysis of the sample, a mixture of 1.00 g of the starch cake, 25 mL of 4 N hydrochloric acid, and 3-4 boiling chips were combined in a covered Erlenmeyer flask and heated to a boil for 7 minutes. The mixture was then cooled to room temperature and then transferred to a 250 mL volumetric flask. The Erlenmeyer flask was rinsed several times with the distilled water and also transferred to the same volumetric flask until it reached the 250 mL mark. Using a 10 mL disposable syringe, 10 mL of the solution in the volumetric flask was drawn. A 13 mm, 0.2 µm Gelman ion chromatography acrodisc syringe filter was then attached to the end of the syringe. The solution was filtered and the collected filtrate was then analyzed on an ICP-AE spectrometer (Perkin-Elmer Optima 3000 DV) that was standardized in accordance with the manufacturer's recommendations. The results were then converted into % bound phosphorus as:

$$\% \text{ bound } P = [\text{ppm Phosphorous} \times \text{dilution factor } (0.25 \text{ L}) \times 100]/\text{Anhydrous sample weight as mg}$$

Table I lists the percent bound phosphorus using the above method.

TABLE I

| Starch Filler | Sample | Inhibition condition | size (µm) | % swelling[a] | Viscosity (cP) | % bound P |
|---|---|---|---|---|---|---|
| Waxy corn[b] | 1 | None: un-inhibited | 15.0[d] | N/A | — | N/A |
| | 2 | 100 ppm epichlorohydrin | 90.5[e] | 603 | >1,000 | N/A |
| Corn[c] | 3 | None: un-inhibited | 15.4[d] | N/A | — | N/A |
| | 4 | None: un-inhibited | No longer granule[e] | — | >1,000 | N/A |
| | 5 | 10% STMP/STP 4 hrs | 22.6[e] | 147 | — | 0.08 |
| | 6 | 5% STMP/STP 24 hrs | 17.6[e] | 114 | — | 0.20 |
| | 7 | 10% STMP/STP 15 hrs | 17.6[e] | 114 | — | 0.40 |
| Waxy rice[b] | 8 | None: un-inhibited | 7.0[d] | N/A | 1.4 | N/A |
| | 9 | None: un-inhibited | No longer granule[e] | — | >1,000 | N/A |
| | 10 | 4% STMP/STP, 3 hrs | 9.8[e] | 140 | 83 | 0.10 |
| | 11 | 8% STMP/STP, 3 hrs | 9.5[e] | 136 | 24 | 0.21 |
| | 12 | 12% STMP/STP, 3 hrs | 9.2[e] | 131 | 16 | 0.33 |

[a]Calculated in percent from (average granule size after cooking)/(average granule size before cooking)
[b]National Starch and Chemical Company, NJ
[c]MELOJEL ® Starch; National Starch and Chemical Company, NJ
[d]Average granule or swelled granule size in slurry, before cooking based on two samples
[e]Average granule or swelled granule size in slurry, after cooking based on two samples Example 3

Formulation of Gelatin-Free Blends

The components to the exemplary (Ex1 and Ex2) and comparative (Com1, Com2, Com3 and Com4) formulations are listed in Table II. To make the blends, all of the dry ingredients (starch, gellan gum, and highly inhibited starch fillers) were added into a bowl and hand mixed. The liquid components (plasticizer, buffer salt, and water) were pre-mixed and then slowly added to the bowl, while blending at speed of 1-2 using a GE food mixer, Model #168949. The mixture was then blended for 2 minutes using speed of 3 to make a uniform dough. The dough was transferred into a food sealer bag, which was then vacuumed and sealed using a Foodsaver Sealer Professional III. The dough was then cooked in a boiling water bath at 95-100° C. for 3 hours, and kneaded by hand at least every 30 minutes to ensure a uniform melt.

TABLE II

| | Ingredient | Ex1 (g) | Ex2 (g) | Com1 (g) | Com2 (g) | Com3 (g) | Com4 (g) |
|---|---|---|---|---|---|---|---|
| Filler | Highly Inhibited Waxy Rice Starch[1] | 5.75 | 0 | 0 | 0 | 0 | 0 |
| | Highly Inhibited Corn Starch[2] | 0 | 5.00 | 0 | 0 | 0 | 0 |
| | MCC[3] (20 μm) | 0 | 0 | 0 | 5.00 | 0 | 0 |
| | TiO$_2$[4] (0.5 μm) | 0 | 0 | 0 | 0 | 5.00 | 0 |
| | Fumed Silica[5] (7 nm) | 0 | 0 | 0 | 0 | 0 | 2.50 |
| Matrix starch | Tapioca starch[6] (PO modified and degraded to 80 water fluidity) | 31.35 | 31.35 | 31.35 | 31.35 | 31.35 | 28.85 |
| Other ingredients | Glycerin[7] | 19.80 | 19.80 | 19.80 | 19.80 | 19.80 | 19.80 |
| | Kelcogel LT100[8] | 3.50 | 3.50 | 3.50 | 3.50 | 3.50 | 3.50 |
| | Kelcogel F[8] | 0.25 | 0.25 | 0.25 | 0.25 | 0.25 | 0.25 |
| | Sodium Phosphate Dibasic, anhydrous[9] | 0.10 | 0.10 | 0.10 | 0.10 | 0.10 | 0.10 |
| Water | Deionized | 39.25 | 40.00 | 45.00 | 40.00 | 40.00 | 45.00 |

[1]Sample 12 from Table I
[2]Sample 7 from Table I
[3]FMC, Avicel PH-F20JP
[4]Spectrum Chemical
[5]Degussa, Aerosil 300
[6]National Starch and Chemical Company, NJ
[7]Spectrum Chemical, CA
[8]CP Kelco, IL
[9]EMD Chemicals Inc., NJ Example 4

Film Preparation

Each cooked melt of formulations from Example 3 was poured separately onto a preheated stainless steel plate (60-105° C.). Films were cast by drawing down the melt on the plate using a preheated (95° C.) stainless steel applicator bar with a 1-2 mm gap. Wet film samples were then cut two minutes after casting.

Example 5

Filled Capsules Preparation

A bench-top manual capsule press (Model 2B, National Starch and Chemical Company) was used to form soft capsules for each films of Example 4. Vegetable oil was used as an example filling. First, the wet film was placed on the bottom piece of the metal die with a small cavity, and a vacuum was used to conform the film to the cavity surface. The vegetable oil was then added to fill the cavity. Another wet film was placed on the top and a top piece of the metal die was used to press against the bottom metal die. The manual press, with air pressure of 140 psi and a die temperature of about 55° C., was used. A capsule was then formed and removed from the press.

Example 6

Film Transparency Measurement

Film transparency was measured using a custom made light transmission device. The device consisted of a laser light source, a film fixture, apertures and a detector. The light source was a laser photo diode with a wavelength of 650 nm. Samples of dry films at 0.50 mm to 0.65 mm thickness were held in a holder with an aperture that eliminated stray and reflected light from the laser light source reaching the detector. A second aperture cropped the solid angle of light passed to the detector. The detector was a silicon photodiode (solar cell). The distance between the sample and the detector was 80 mm. The voltage signal from the detector was measured by a Fluke 45 digital multi-meter. The entire laser, sample, detector optical train was enclosed to minimize effects of stray and ambient light on the measurement. Film transparency was measured as the ratio of intensity of transmitted light over the incident light. The average film transparency (in percent) of the formulations, based on at least 5 measurements, is listed in Table III.

Example 7

Capsule Burst Strength Measurement

Capsule burst strength was measured with Texture Analyzer TZ-XT2, Texture Technologies Corp. A capsule was placed on the flat platform of the Texture Analyzer, and a probe was discharged at 5 mm/min to impact the capsule. The force required to rupture the capsules made from the formulations are listed on Table III.

TABLE III

| Formulation | Ex1 | Ex2 | Com1 | Com2 | Com3 | Com4 |
|---|---|---|---|---|---|---|
| Filler | Sample 12 | Sample 7 | none | MCC | TiO$_2$ | Silica |
| Filler Refractive index[z] | 1.53 | 1.53 | N/A | 1.53 | 2.55-2.70 | 1.54 |

TABLE III-continued

| Formulation | Ex1 | Ex2 | Com1 | Com2 | Com3 | Com4 |
|---|---|---|---|---|---|---|
| Transparency (%) | 75 | 59 | 84 | 15 | 6 | 29 |
| Burst Strength (g) | 1926 | 2296 | 1326 | 1375 | 1300 | 738 |

[2]Pulp and Paper: Vol. 1, J. P. Casey, Interscience Publishers, New York, 1952, p 474.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

The invention claimed is:

1. A composition comprising:
   a) at least one highly inhibited granular starch filler, wherein said filler swells less than 150% after cooking at 95-100° C. for 30 minutes;
   b) at least one matrix starch selected from the group consisting of native starch and modified starch, wherein modified starch is modified physically, chemically and/or by hydrolysis, and wherein starches modified chemically are selected from the group consisting of hydroxyalkylated starches and succinated starches, and starches modified physically are modified by a method selected from extrusion, spray-drying, drum-drying, agglomeration, pregelatinization and mixtures thereof, wherein the matrix starch comprises from about 40 to about 95 weight percent of the total dry composition; and
   c) at least one plasticizer;
   wherein said composition is a film having a thickness of about 0.50 mm to about 0.65 mm, has a transparency greater than 70%.

2. The composition of claim 1, wherein the highly inhibited granular starch filler is made from a starch selected from the group consisting of waxy rice, corn, high amylose, waxy maize, tapioca, wheat, sago, rice, and potato starch.

3. The composition of claim 1, wherein the matrix starch is a modified starch.

4. The composition of claim 1 further comprising a gum or hydrocolloid.

5. The composition of claim 1 further comprising at least one salt buffer, emulsifiers, humectants, surfactants, gelling agents, preservatives, embrittlement inhibiting agents, disintegrants, colorants, taste masking agents, permeation enhancers and surface modifying agents.

6. The composition of claim 1, wherein the highly inhibited starch filler comprises from about 0.01 to about 20 weight percent of the total dry composition.

7. The composition of claim 1, wherein the plasticizer comprises from about 5 to about 50 weight percent of the total dry composition.

8. The composition of claim 4, wherein the gum or hydrocolloid comprises up to about 10 weight percent of the total dry composition.

9. The composition of claim 5, wherein the salt buffer, emulsifiers, humectants, surfactants, gelling agent, preservatives, embrittlement inhibiting agents, disintegrants, colorants, taste masking agents, permeation enhancers and surface modifying agents is up to about 10 weight percent of the total dry composition.

10. The composition of claim 1, wherein said composition contains no gelatin.

11. The composition of claim 1 further comprising up to 1 weight percent of gelatin, based on the total dry weight.

12. The composition of claim 1, wherein said composition being in the form of a soft capsule.

13. A soft capsule shell composition comprising:
   a) a highly inhibited granular waxy rice starch filler, wherein said filler swells less than 150% after cooking at 95-100° C. for 30 minutes;
   b) a hydroxypropylated starch, wherein the starch comprises from about 40 to about 95 weight percent of the total dry composition; and
   c) a plasticizer;
   wherein said composition when cast as a film having a thickness of about 0.50 mm to about 0.65 mm has a transparency greater than 70%.

14. The shell composition of claim 13 further comprising a salt buffer.

15. The shell composition of claim 14 further comprising a gum or hydrocolloid.

16. The shell composition of claim 13, wherein said composition contains no gelatin.

17. A soft gel capsule system wherein the shell is made from the composition of claim 13 and the fill material is a pharmaceutical, nutraceutical or food agent.

18. The composition of claim 1, wherein the matrix starch has a water fluidity in the range of about 30 to about 90.

* * * * *